(12) United States Patent
Kaehne

(10) Patent No.: US 9,441,218 B2
(45) Date of Patent: Sep. 13, 2016

(54) SALT TOLERANT LUCERNE

(71) Applicant: Springbrook Nominees Pty Ltd, Unley (AU)

(72) Inventor: Ian David Kaehne, Belair (AU)

(73) Assignee: SPRINGBROOK NOMINEES PTY LTD, South Australia (AU)

( * ) Notice: Subject to any disclaimer, the term of this patent is extended or adjusted under 35 U.S.C. 154(b) by 335 days.

(21) Appl. No.: 13/959,052

(22) Filed: Aug. 5, 2013

(65) Prior Publication Data

US 2014/0047573 A1    Feb. 13, 2014

(30) Foreign Application Priority Data

Aug. 7, 2012  (AU) .............................. 2012903373

(51) Int. Cl.
- C12N 15/01 (2006.01)
- C12N 15/82 (2006.01)
- A01H 5/12 (2006.01)

(52) U.S. Cl.
CPC ................ *C12N 15/01* (2013.01); *A01H 5/12* (2013.01); *C12N 15/8273* (2013.01)

(58) Field of Classification Search
None
See application file for complete search history.

(56) References Cited

U.S. PATENT DOCUMENTS

| 6,005,165 A | 12/1999 | Dobrenz et al. |
| 7,067,721 B2 | 6/2006 | Velde |
| 2003/0046729 A1 | 3/2003 | Blumwald |

FOREIGN PATENT DOCUMENTS

WO    99/53016 A2    8/1999

OTHER PUBLICATIONS

Winicov. Characterization of salt tolerant alfalfa (*Medicago saltiva* L.) plants regenerated from salt tolerant cell lines. Plant Cell Reports. 1991. 10: 561-564.*
Al-Khatib MM, et al. Between and within cultivar variability in salt tolerance in lucerne, (*Medicago sativa* L.). Genetic Resources and Crop Evolution, 1994;41:159-164.
Li W, et al. The Vacuoler Na+/H+ Antiporter Gene SsNHX1 from the Halophyte Salsola soda Confers Salt Tolerance in Transgenic Alfalfa (*Medicago sativa* L.). Plant Mol Biol Rep, 2011;29:278-290.
Peel MD et al.; Screening for Salinity Tolerance in Alfalfa: A Repeatable Method; Crop Sci. (2004) 44:2049-2053.

* cited by examiner

Primary Examiner — Shubo (Joe) Zhou
Assistant Examiner — Ashley K Buran
(74) Attorney, Agent, or Firm — Henry D. Coleman; R. Neil Sudol

(57) ABSTRACT

A salt tolerant *Medicago sativa* plant designated as "Silverosa" representative seed of which having been deposited under NCIMB Accession No. 41909, NCIMB Accession No. 41910 and NCIMB Accession No. 41911.

8 Claims, No Drawings

SALT TOLERANT LUCERNE

FIELD OF THE INVENTION

This invention relates to a method of producing a salt tolerant lucerne, a salt tolerant lucerne, plant parts thereof, and a method of growing lucerne in saline soil.

BACKGROUND OF THE INVENTION

Salinity is a significant agricultural problem, often associated with irrigation in arid or semi arid regions, particularly where there is inadequate subsurface drainage of excess rain and irrigation water. Irrigation water carries with it salts and where these are not drained, there remains a build up of salt after evaporation, or drainage of saline water into depressions.

Significant areas of the world are affected and in 1980 FAO/UNESCO estimated that there were about 3,230,000 km$^2$ of saline land world wide, and for each continent this was estimated as follows (in10$^6$ ha); Australia, 84.7, Africa, 69.5, Latin America, 59.4, Near and Middle East, 53.1, Europe, 20.7, Asia and Far East, 19.5, Northern America, 16.0.

The United States Department of Agriculture estimates that, worldwide, 10 million hectares of arable land is lost to irrigation salinity every year. In Australia approximately 2.4 million hectares of land is affected by salinity and 5.7 million hectares of productive land is at risk. It has been estimated that the area of salt-affected land in Australia could increase six-fold in the next 30 to 50 years.

Engineering solutions such as reclamation, drainage and improved irrigation practices can reduce the severity and spread of salinization in many regions but costs of these practices are generally considered prohibitive.

An alternative approach for marginally affected land is to develop plants that are more salt tolerant and economically useful that can still be used in compromised soil. The benefit of this approach is that otherwise non-productive land can be used commercially. It also has the additional benefit of slowing movement of saline drainage water, increasing evapotranspiration and reducing and maintaining watertable levels below the soil surface, thereby slowing further deterioration.

Lucerne (*Medicago* spp.) is a perennial legume having a deep tap root, a number of stems extend upward from a woody crown to a height of up to about a metre, and bearing an abundance of leaves. It is widely used as livestock feed. New stems develop when older ones mature or have been removed by cutting or grazing. Reproduction is mainly via cross-fertilization by pollinators such as bees, but self-pollination may also occur.

Lucerne is mainly tetraploid, with 32 chromosomes, although some less vigorous diploid species are also known. Lucerne species comprise ecotypes, being population complexes adapted to particular environments in which the species is found with sufficient variability in the population to enable adaptation to change within a range of environmental parameters.

Apart from in the tropics, lucerne is widely adapted to temperature and soil conditions, however, all commercially available cultivars have poor salt tolerance. Being a widely used forage species, it is desirable to have a salt tolerant lucerne because there are large areas of potential forage pasture that could be developed but for the lack of a salt tolerant lucerne.

Whilst variations between ecotypes do exist, in general, forage yield of lucerne decreases 7.3% for each dSm$^{-1}$ (~11 mM NaCl) increase above a threshold of 2.0 dSm$^{-1}$ (~22 mM NaCl) (Johnson et al 1992 "Genetic and phenotypic relationships in response to NaCl at different development states of alfalfa" Thert Appl Genet Volume 83, Numbers 6-7, 833-838). Seedling lucerne yield is decreased by 50% at 8.9 dSm$^{-1}$ (~97 mM NaCl) (Mass & Hoffman, 1977—Crop salt tolerance current assessment J. Irrig Drainage Div. Am. Soc. Civil Eng. 103:115-134). In addition to variation between lucerne ecotypes, these values are dependent on soil conditions, so that on less well-drained soil the salt tolerance limit of lucerne plants may be lower.

Salinity research in lucerne has focussed in large part on seed germination and seedling establishment in the presence of NaCl. This research is however not representative of the natural habitat of most agricultural lucerne plants (Peel et al., (2004) Crop Sci 44:2049-2053). Less research has been conducted on persistence, yield, grazing tolerance, or other measures of agronomic suitability of mature lucerne plants in a saline environment and none that the inventor is aware of where the grazing tolerance has been assessed at high NaCl levels of 150 mM NaCl (about 1.37 dS/m), or greater.

There have been a number of attempts at developing salt tolerant lucerne plants. One variety resulting from such research is known as "Salado" (available from America's Alfalfa, Nampa, Id., USA) details of which are described in US 6005165.

The difficulty with this variety however is that whilst the seed is described as being capable of germinating at high salt levels, germination is only one aspect exhibited by a truly salt tolerant plant. Germination is very much more relevant for forage plants that are annual and self seeding, whereas for lucerne which is a perennial plant the self seeding is of less importance, and other characteristics such as its persistence and grazing resistance while growing in saline conditions are more critical. The "Salado" variety of lucerne was introduced on the Australian market in late November 1999 but has not had much commercial success because of reduced yields and lack of significantly higher salt tolerance when exposed to a rising salt level (approximately 2 dS/m per week) as established plants in comparison with other varieties not marketed as salt tolerant (see Peel et al., (2004)).

Another salt tolerant lucerne is described in U.S. Pat. No. 7,067,721 being a winter dormant variety, but no corresponding commercial plant has been marketed. The salinity tolerance of this lucerne population was tested at 115 mM NaCl.

Neither Peel et al., nor U.S. Pat. No. 7067721 describe the growth of lucerne in high saline environments for extended periods of time, nor do these documents show, under the same conditions, the recovery of lucerne by regrowth after cutting off mature stem growth. Also it is essential that a salt tolerant lucerne be palatable to livestock.

Salinity is a soil condition characterized by a high concentration of soluble salts. Soils are classified as saline when the ECe is 4 dS/m or more (131-USDA-ARS. 2008. Research Databases. Bibliography on Salt Tolerance. George E. Brown, Jr. *Salinity Lab. US Dep. Agric., Agric. Res. Serv.* Riverside, Calif.,) which is equivalent to approximately 40 mM NaCl or more and generates an osmotic pressure of approximately 0.2 MPa. This definition of salinity derives from the ECe that significantly reduces the yield of most crops.

The effect of salt on plants is multivarious and complex but the effects are usually assigned to two general categories.

Firstly there is an osmotic effect, whereby plants are unable to take up sufficient water. Secondly there is a toxicity effect whereby the dominant ion, typically Na but also Cl impact on particular metabolic and physiological processes.

Several cellular and plant mechanism are affected by salinity, these have been reviewed in Munns and Tester (2008 Annu Rev Plant Biol 59:651-681). The particular plant processes where salinity might impact or salinity tolerance arise might be summarised as follows 1) sensing and signalling in roots, 2) shoot growth, 3) photosynthesis, 4) accumulation of sodium in shoots, 5) accumulation of sodium in vacuoles and 6) accumulation of organic solutes.

It might reasonably be expected that altered genes or mutations in the complex genetics of any of these processes will impact on salt tolerance, and very likely that several of these together might provide cumulative effects and thus enhance tolerance. A simple genetic alteration would not be expected to result in enhanced tolerance.

Problems associated with salinity in agriculture have been experienced for millenia, and where cultivable land had become short suitable efforts to breed salt tolerant plants using conventional means have been attempted. There has been limited success with this and the levels of tolerance achieved are limited. This result might be expected because of the complexity particularly of the toxicity effects of the high levels of salts as referred to above, and the polyploid nature of many agricultural plants.

In more recent times attempts have been made using recombinant means particularly by altering the transport of salts, but also by altering the targets alleviating the effects and addressing quite a range of targets to do so. This recombinant approach is generally considered to hold out most promise.

SUMMARY OF THE INVENTION

The inventor has devised a simple method of selecting for tolerance to high level of salt in lucerne, and has discovered surprisingly that relatively high numbers of salt tolerant plants can be achieved by mutagenesis. The salt tolerance characteristic so achieved can be transferred by conventional crossing techniques to other lucerne varieties.

A more specific aspect of the invention arises from the finding that it is possible to obtain a population (or ecotype) of lucerne plants capable of growing whilst being watered at salt concentrations of 150 mM NaCl or above over an extended period, in glasshouse conditions. Thus a first aspect of the present invention provides for a lucerne plant, within a population, that is capable of growing in a growth medium and being watered with at least 150 mM NaCl over a period of at least four months. Of considerable importance is that these plant are able to regrow after at least one, two and more particularly three or more harvests. This has proven to be a distinguishing characteristic of survivors over non salt tolerant populations. In a preferred embodiment the leaves of the lucerne plant of this invention when grown in saline conditions are not excessively salty. In a most preferred form the taste is not perceptively different to those grown with no added NaCl, and in another form the leaves have a sodium level of less than 4.25, 4, 3.75, 3.5, 3.25, 3, 2.75, 2.5, 2.4%, in a specific form the leaves have a sodium level less that 3.5%, and in a preferred form the leaves have a sodium level of less than 3.0%, and in a most preferred form the leaves have a sodium level of less than 2.75, or 2.5%.

Experiments to date show that plants in the lucerne population of the present invention are able to withstand at least about 200 mM and at times about 250 mM. There are also some survivors at about 300 mM, but the numbers of tolerant plants that survive a plurality of harvests at that level in the present population is quite low.

The proportion of the population capable of withstanding being watered over that period is at least 10%, but more preferably at least 15, 20, 25, 30, 35, 40, 45 or 50% of the population. This might be tested in the presence of 150, 200, or 250 mM NaCl.

Salt tolerant mutants of the present invention are generally able to grow when watered with the set level of salt in the water for an indefinite period, after an initial period for about 4 months and/or after two harvests. The test might be conducted for at least 5, 6, 7, 8, 9 or 10 months. Alternatively or additionally the test might be conducted for at least 2, 3 or 4 harvests.

The invention might also be said to reside in seeds derived from the plant of the first aspect or from plant parts of said lucerne plant.

In a second aspect the invention could be said to reside in a *Medicago sativa* designated Silverosa, wherein the seed is selected from the group of samples which have been deposited in the NCIMB depositary and have been assigned accession numbers NCIMB 41909, NCIMB 41910 or NCIMB 41911. In a further alternative of this specific aspect of the invention the deposit might be NCIMB 41909. In a yet further alternative of this specific aspect the invention the deposit might be NCIMB 41910. In a still further alternative of this specific aspect the invention the deposit might be NCIMB 41911.

In a further alternative the invention might be said to reside in a plant or plant parts produced by growing the seed of the second aspect of this invention, or a plant with all the physiological and morphological characteristics of the plant of the second aspect of this invention. In yet another alternative the invention might be said to reside in a plant, plant parts, or seed produced by self pollinating a plant grown from a seed of the second aspect of this invention.

In a third aspect the invention could be said to reside in a method of producing a salt tolerant lucerne cultivar Silverosa derivative lucerne plant. The method of this third aspect comprises (a) crossing a plant which is produced by growing a lucerne seed deposited as any one the group comprising deposit accession numbers NCIMB 41909, NCIMB 41910 and NCIMB 41911 with a second lucerne plant to produce progeny lucerne seed; and (b) growing said progeny seed to produce a lucerne cultivar Silverosa derivative plant. The method might further comprise (c) crossing the lucerne cultivar Silverosa derivative lucerne plant of (b) with itself or a third lucerne plant to produce a second lucerne Silverosa derivative lucerne progeny seed; and (d) growing the second lucerne progeny seed of (c) to yield a second lucerne cultivar Silverosa derivative lucerne plant. Steps (c) and (d) may be repeated at least one time to generate at least an additional alfalfa cultivar Silverosa derivative lucerne plant.

In a fourth aspect the invention might be said to reside in a method of producing a salt tolerant lucerne plant comprising the step of taking seeds of a parent population of lucerne seeds, germinating said seeds to plants in a container of growing medium, maintaining moisture levels in said growing medium by irrigation with water having at least 150 mM NaCl, or another salt with an equivalent dS/m value of at least about 13.7 dS/m, harvesting said plants at least two times and maintaining said plants for at least 4 months, selecting at least one surviving plants and crossing said plant either with a second surviving plant or a plant of another lucerne variety to produce F1 progeny seeds, germinating said F1 progeny seed into an F1 progeny plant and growing the F1 progeny plant a container of growing medium, maintaining moisture levels in said growing medium by irrigation with water having at least 150 mM NaCl, or equivalent of another salt, cutting back said plants at least twice and maintaining said plants for at least 4 months, selecting surviving plants. Preferably the parent population is a diploid variety, and preferably seeds of the parent population have been subjected to mutagenesis before being germinated. The method also preferably comprises crossing a survivor with a tetraploid lucerne plant to produce the F1 progeny, which progeny are selected for salt tolerance by watering with at least 150 mM NaCl, or equivalent amount of the other salt. Such other salt might be selected from the group consisting of K, Ca and Mg and these might be presented as a chloride, sulphate, nitrate, bicarbonate or carbonate.

In a fifth aspect the invention might be said to reside in a process of introducing a desired trait into a Silverosa lucerne comprising: (a) crossing Silverosa plants grown from Silverosa seed, representative seed of which has been deposited under NCIMB Accession Nos: 41909, NCIMB 41910 and NCIMB 41911, with plants of another lucerne variety that comprise a desired trait to produce F1 progeny plants, wherein the desired trait is selected from the group consisting of male sterility, site-specific recombination, increased transformability, abiotic stress tolerance, herbicide resistance, insect resistance, disease resistance, altered phosphorus, altered antioxidants, altered fatty acids, altered essential amino acids and altered carbohydrates; (b) selecting F1 progeny plants that have the desired trait to produce selected F1 progeny plants; (c) crossing the selected progeny plants with the Silverosa plants to produce backcross progeny plants; (d) selecting for backcross progeny plants that have the desired trait and physiological and morphological characteristics of lucerne variety Silverosa to produce selected backcross progeny plants; and (e) repeating steps (c) and (d) three or more times in succession to produce selected fourth or higher backcross progeny plants that comprise the desired trait and all of the physiological and morphological characteristics of lucerne variety Silverosa.

By "a plant derived from the seed deposited as any one of NCIMB Accession Nos: 41909, NCIMB 41910 and NCIMB 41911", it is meant a plant that is grown directly from the seed deposited as NCIMB Accession Nos: 41909, NCIMB 41910 and NCIMB 41911 respectively, or a plant that is obtained indirectly from a plant grown from the seed deposited as NCIMB Accession Nos: 41909, NCIMB 41910 and NCIMB 41911. Plants obtained indirectly from a plant grown from the seed deposited as NCIMB Accession Nos: 41909, NCIMB 41910 and NCIMB 41911 may be grown from a vegetative cutting, seed, callus or tissue culture obtained from a plant or plant part grown from the seed deposited as NCIMB Accession Nos: 41909, NCIMB 41910 and NCIMB 41911 or a clonal plant thereof, or alternatively a salt tolerant plant resulting from the crossing with the lucerne plant with other agronomic characteristics.

The present invention contemplates using the Silverosa plant, or part thereof, or an alfalfa plant having the physiological and morphological characteristics of the Silverosa plant, as a source of pasture forage, hay, haylage, greenchop and dehydrated products.

The principal physiological and morphological characteristic of the lucerne plant is tolerance to being watered with salt, (particularly NaCl) concentrations of 150 mM, 200 mM, 250 mM or above for at least two harvests, and non salty taste to leaves when so watered. The leaves having less than 4.25, 4, 3.75, 3.5, 3.25, 3, 2.75, 2.5, 2.4%, Na content. Secondary physiological and morphological characteristics are moderate to very high resistance to intense continuous grazing, with a propensity to develop a broad crown ranging from moderate to very strong, high resistance or tolerance to leaf and stem diseases, high resistance or tolerance to pathogenic nematodes, high resistance or tolerance to crown and root diseases, high drought tolerance, and forage quality being high to very high. Also a leaf size being intermediate to large, with moderate to very strong stem branching and intermediate to very high stem density.

The present invention contemplates using the Silverosa lucerne plant, or part thereof, or a lucerne plant having the salt tolerance characteristics of the Silverosa lucerne plant, as a source of breeding material for developing or producing a Silverosa derivative plant in an lucerne breeding program using plant breeding techniques. Plant breeding techniques useful in the developing or producing lucerne plants include, but are not limited to, single seed descent, modified single seed descent, recurrent selection, reselection, mass selection, bulk selection, progeny testing, backcrossing, pedigree breeding, mutation breeding, restriction fragment length polymorphism enhanced selection, genetic marker enhanced selection, and transformation. Plant breeding techniques are known to the art and have been described in the literature. The present invention also encompasses the Silverosa derived plant developed or produced by these methods, that may additionally have the secondary physiological and morphological characteristics of a Silverosa plant.

As used herein, the term "plant" includes, but is not limited to, plant cells, plant protoplasts, plant cell tissue cultures from which lucerne plants can be regenerated, plant calli, plant clumps, and plant cells that are intact in plants or parts thereof. "Plant part" includes, but is not limited to, embryos, pollen (pollen grains), ovules, seeds, flowers, pods, leaves, roots, root tips, anthers, and the like.

One may obtain lucerne plants according to the present invention by directly growing the seed Silverosa or by any other means. A lucerne plant having all of the physiological and morphological characteristics of Silverosa can be obtained by any suitable methods, including, but not limited to, regenerating plants or plant parts from tissue culture or cuttings. The scope of the present invention is not limited by the method by which the plant is obtained.

DETAIL DESCRIPTION OF EXEMPLIFIED EMBODIMENTS OF THE INVENTION

EXAMPLES

Methods
Lucerne Plants
Lucerne cv Jindera, (Australian Plant Breeders Rights Journal vol 10(3) p27) (1997)
Lucerne cv Silverado (Australian Plant Breedrs Rights Application 2004/201),
Lucerne cv Sceptre, (Australian Plant Breeders Rights Journal vol 8(1) p16) (1995)

Lucerne cv Septre is available from the National Medicago Genetic Research Centre, South Australian Research and Development Institute. Lucerne cv Jindera is also available from the South Australian Research and Development Institute, Glen Osmond, South Australia, Lucerne cv Silverado is available from Springbrook Nominees Pty Ltd, Belair, South Australia.

Mutagenesis

Germination. Seeds were placed on blotting paper at ambient temperature for 36 hours. The blotting paper was saturated in the Hydrazine Chloride solution (below).

Preparation of Hydrazine Chloride Solution. The hydrazine chloride solution was prepared after the method of Kain et. al., (1968) Heredity (Edinburgh) 23(2):247-256. The germinating seeds were treated with a 0.1 M hydrazine chloride solution buffered with sodium borate to pH8.5 with 0.1N sodium hydroxide using phenolphthalien indicator.

Other chemical mutagens might also be used, examples of which include base analogues (for example bromouracil, aminopurine), intercalating agents (for example acridine orange, proflavin, ethidium bromide) deaminating agents, alkylating agents, and acridine derivatives. One example of a commonly used alkylating agent is ethylmethane sulfonate (EMS). Alternatively physical mutagens such as Fast Neutron Bombardment (FNB), γ ray, Ultraviolet light and X rays can be used.

Selection

Germinated seeds were planted, and initially grown in water without added salt. Thus somewhat more mature plants were subjected to testing. However, it might be desired to apply NaCl from the initial planting of the germinated seeds.

Preferably one level of salt is used, being the amount of the test, and this might be from 150 mM, to 350 mM, preferably at least 200 mM, or at least 250 mM, and for an extended time of from, for example, 60 days up to 120 days or 250 days. Most relevantly the selection in a tray is different to growth in a saline field, and whilst in field experiments it becomes apparent very quickly that there is a difference in salt tolerance, generally under current protocol, when grown in trays in a glasshouse the difference does not become visually apparent until after the plants have been harvested twice, and perhaps for a more definite result three, or four times.

Alternatively but less preferred is to increase the NaCl concentration, thus the initial salt concentration might be about 350 mM, after a week the salt concentration could be raised up to about 700 mM for about 60 days. Thereafter plants are watered with no additional salts.

The initial concentration might be about 90 mM and then increased to about 450 mM together for a period of 3 months, after which treatment with salt is discontinued.

Alternatively the initial concentration is started at about 55 mM and increased every week to about 520 mM over a period of about a month and then maintained for approximately one month.

In a further alternative the salt treatment comprises an initial concentration of 250 mM being increased to about 520 mM over a period of 6 weeks and maintained at this level for a further 6 weeks.

It will be understood that NaCl is used because it is generally considered to be the salt to have most impact in agriculture and is gerenally used as a standard in research. However in selections it is possible to use other salts, for example, those based on potassium (K), calcium (Ca) or magnesium (Mg), to provide for soil conditions with comparable levels of saturated conductivity that the levels of NaCl has provided for.

Breeding Methods

As will be appreciated the present invention is not limited to the specific plants and varieties specifically disclosed in this specification, but also comprises the use of these plants in methods of breeding lucerne.

Open-Pollinated Populations

The improvement of open-pollinated populations of lucerne depends essentially upon changing gene-frequencies towards fixation of favourable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by pollinators with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure, such as by growing with exposure to high salt concentrations. The outcome is an improved population that is indefinitely propagable by random-mating within itself in isolation. Second, a synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and article.

Mass Selection

In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population. This has been the procedure adopted by the present invention.

Glasshouse Procedures.

Seeds were sown in duplicate flat trays, being 40 cm×30 cm by 10 cm deep, containing sandy loam soil. These were maintained under glasshouse conditions.

Control and experimental seeds were each sown in rows in each duplicate tray. Trays were watered with deionized water, to maintain an adequate moisture. Plants generally germinated in 14 to 21 days, and were grown until they were about 3 cm tall before the experimental trays were watered with NaCl solutions.

Harvesting of plants entailed cutting plants down to a height of approximately 1 cm.

Example 1

Selecting Salt Tolerance

| Step | sel* | Int* | Procedure |
|---|---|---|---|
| 1 | | | Germination of approximately 60,000 Jindera lucerne seeds in 84 Petri dishes on moist blotting paper |
| 2 | | | Day 2, Treatment with hydrazine chloride commenced at 24 hr from commencement of germination and continued for 36 hrs |

-continued

| Step | sel* | Int* | Procedure |
|---|---|---|---|
| 3 | | | Day 4, Treated germinated seeds transferred to trays of soil and lightly covered with soil and watered daily with tap water |
| 4 | 1 | | Day 30, Commenced salinity treatment by submerging trays (with drain holes) in a bath of 20,000 ppm (342 mM NaCl) for 10 minute daily and then allowing drainage of excess solution. |
| 5 | | | Day 42, The concentration of the saline solution was increased to 40,000 ppm (684 mM) NaCl |
| 6 | | | 56 days after commencing the saline treatment 14 plants which were still actively growing were transplanted into non-saline potting soil. 5 plants survived to maturity |

*Sel denote Selection, Int denotes Intercross

Discussion.

The initial mutagenesis on the diploid variety "Jindera" gave a high level of salt tolerant progeny, so that at step 6, there were 5 survivors of the salt selection, with the use of an initial approximately 60,000 seeds. The 5 survivors are each independent mutations that are able to grow at over 690 mM NaCl for 2 weeks. This is a frequency of 1/12000, which is readily screened using the methods set out herein.

The variety Jindera was used as the initial selection species. However other diploid populations could equally have been used.

It can be seen that with a diploid plant, that the frequency of achieving salt tolerance is well within a range for which selection of reasonable numbers of seeds can be screened.

Example 2

Crossing the Salt Tolerant Genotype into Agronomically Preferred Plants

Breeding Agronomically Acceptable Lucerne Plants

| Step | sel* | Int* | Procedure |
|---|---|---|---|
| 7 | | 1 | a. Inter-crossing 5 survivors, and<br>b. Inter-crossed 5 survivors with parent clones of the variety "Silverado" |
| 8 | 2 | | Commenced selection for salinity tolerance in approximately 2000 seedlings grown from Inter-crossing cycle 1.3 batches of seedlings were screened<br><br>Batch  Sowing date  Treatment Period<br>1  24 Mar. 2001  7 Apr. 2001 to 18 Apr. 2001<br>2  3 Apr. 2001  4 May 2001 to 9 Jun. 2001<br>3  8 Jul. 2001  1 Aug. 2001 to 23 Dec. 2001<br>The treatment solution concentrate was 20,000 ppm (342 mM) NaCl and the same immersion procedure was use as in selection cycle #1 43 seedlings were selected. 17 were from inter-crosses of the 5 selections from cycle 1 and 26 were from crosses of the 5 original selections with "Silverado". The variety "Sceptre" was used as a control. No "Sceptre" seedlings tolerated the saline treatment |
| 9 | | 2 | The 43 selections from selection cycle 2 plus the 5 original selections were inter-crossed in the glasshouse by hand-crossing and seed harvested from the 43 individual parent plants from selection step 2. |
| 10 | 3 | | Sowed progeny from inter-crossing cycle 2 and commenced screening of seedlings using the immersion technique of screening cycle 1 on 12 Aug 2002. The initial saline solution concentration was 5000 ppm (86 mM) NaCl and which was increased linearly to 25,000 ppm (428 mM) NaCl until 7 Nov 2002 and then maintained at this level until the treatment was terminated on 17 Nov 2002.<br>On 27 Nov 2002 120 seedlings least affected by the saline treatment were selected and transplanted to non-saline soil in pots. The variety "Sceptre" was used as a control. No "Sceptre" seedlings tolerated the saline treatment. |
| 11 | | 3 | The 120 selections from selection cycle 3 were inter-crossed in the field and harvested individually. |
| 12 | 4 | | Sowed progeny from intercrossing cycle 3 and commenced screening of the seedlings using the immersion technique of screening cycle 1 on 27 Sep 2003. The initial saline solution concentration was 3000 ppm (57 mM) NaCl and was increased linearly in weekly steps to 30,000 ppm (513 mM) NaCl on 1 Nov. 2003 and maintained at this level until 6 Dec. 2003 when 120 seedlings least affected by the saline treatment were selected and transplanted to non-saline soil in pots. The variety "Silverado" was used as a control. No "Silverado" seedlings tolerated the saline treatment. |
| 13 | | 4 | The 120 selections from selection cycle 4 were inter-crossed in the field and harvested individually |
| 14 | 5G | | Seed from inter-crossing cycle 4 was sown in trays and screening of the seedlings was commence in July 2004 |

-continued

| Step | sel* | Int* | Procedure |
|---|---|---|---|
| | | | using the immersion technique of screening cycle 1. The initial saline solution concentration was 15,000 ppm (257 mM)NaCl. It was increased linearly in weekly steps of 1000 ppm to 30,000 ppm (513 mM) NaCl and maintained at this level until December 2004 when 120 seedlings least affected by the salinity treatment were selected. The variety "Silverado" was used as a control. No "Silverado" seedlings tolerated the saline treatment, (proceed to step 16: intercrossing cycle 5G) |
| 15 | 5F | | Seed from Inter-crossing Cycles 3 and 4 was sown in a saline field (in Queensland, Australia). Each single plant progeny was sown in 5 m row plots at a seedling rate of 1 g (approximately 400 seeds) per row. The progeny rows were inter-seeded with rows of the variety "Silverado" as a control. In May 2005, 216 plants with the best production were selected from rows within the trial adjacent to "Silverado" rows where no control plants had survived (proceed to step 18; Inter-crossing cycle 5F) |
| 16 | | 5G | The 120 selections from selection cycle 5G (step 14) were inter-crossed in the field and harvested individually (proceed to step 17; selection cycle 6F) |
| 17 | 6F | | Seed from Inter-crossing cycle 5G was sown in a saline field (in Queensland). Each single plant progeny was sown in 5 m row plots at a seedling rate of 1 g (approximately 400 seeds) per row. The progeny rows were inter-seeded with rows of the variety "Silverado" as a control. In May 2006, 72 plants with the best production were selected from rows within the trial adjacent to "Silverado" rows where no control plants had survived (Proceed to step 19 Inter-crossing cycle 6F). |
| 18 | | 5F | The 216 selections from Selection cycle 5F (step 15) were inter-crossed in the field and harvested individually (proceed to step 20, selections step 7F) |
| 19 | | 6F | The 72 selections from selection cycle 6F (Step 12) were inter-crossed in the field and harvested individually. A bulk sample of this harvest is seed depositary sample SN 2011/1, being a 72 parent plant synthetic variety. |
| 20 | 7F | | The progeny of inter-crossing cycle 5F were sown in a saline field (in Queensland, Australia). Each progeny was sown in a hill plot. The hill plots were sown on a 1 m × 1 m grid with the middle hill of each cluster of 9 plots (3 × 3) sown with the variety "Silverado" as a control. In September 2008 113 plants with the best production were selected from hill plots adjacent to control plots where no control plants had survived (Proceed to step 21, inter-crossing cycle 7F) |
| 21 | | 7F | The 113 selections from selection cycle 7F (step 20) were inter-crossed in the field and harvested individually. A bulk sample of this harvest is seed depositary sample SN 2011/2 |
| 22 | 8F | | Seed from intercross cycles 5G, 5F and 6F were sown (in 2007) in progeny plots in a saline field (in Queensland, Australia). Each plot consisted of 5 5 m rows spaced 20 cm apart and was sown with 5g of seed per plot. In September 2009 the 60 most salt-tolerant plots were selected. |
| 23 | | 8F | the 60 plots selected in selection cycle 8F were intercrossed in the field and each plot was harvested individually. A bulk sample of this harvest is seed deposit sample SN2011/3 |

*Sel denote Selection, Int denotes Intercross

Discussion.

The mutagenesis is followed by several crossing steps, to firstly reduce the number of mutations not related to salt tolerance and to introduce the salt tolerance characteristic into a tetraploid variety with preferred agronomic characteristics. In the present example the lucerne variety "Silverado" was chosen as a suitable agronomic background, although others might also be chosen depending on specific agronomic characteristic that might be desired.

These might be used in an intercrossing regime with elite Australian varieties such as Aurora, Genesis, Trifecta, and Pegasis. Alternatively these might be used in an intercrossing regime with elite European varieties such as Carmen, Lodi, Luignano, Magali, Melissa and Monica. In a further alternative these might be used in an intercrossing regime with elite North American varieties such as Expedition, Liberator, Mecca III, Sedona, Sequoia, Spredor 4, and Sutter.

Deposits Made Under the Budapest Treaty

Seeds were deposited the NCIMB depositary in Ferguson Building, Craibstone Estate, Bucksburn Estate, Bucksburn, Aberdeen, Scotland, United Kingdom under the terms of the Budapest Treaty

| Sample | Date of Deposit | Accession Number |
|---|---|---|
| SN 2011/1 | 6 Dec. 2011 | NCIMB 41909 |
| SN 2011/2 | 6 Dec. 2011 | NCIMB 41910 |
| SN 2011/3 | 6 Dec. 2011 | NCIMB 41911 |

Example 3

Plant Characteristics

Field Trials for testing plant characteristics and seed yield Three different plots of the three representative Silverosa plants (SN 2011/1, 2011/2 and SN 2011/3) were planted in 2011 near Bordertown South Australia, in non-saline soil, adjacent to the parent plant Silverado to compare plant characteristics and seed yield. This provided as means of determining whether the Silverosa plants were stable and provided an in-field comparison of seed yield.

Plant Descriptions

All relevant tests meet the minimum standards set out in "Standard Tests to Characterize Alfalfa Cultivars, Third Edition (amended 2004)" Fox et al., (Eds) published by North American Alfalfa Improvement Conference.

The principal physiological and morphological characteristic of the lucerne plant is tolerance to being watered with salt, (particularly NaCl) at concentrations of 150 mM, 200 mM, 250 mM or above for at least two harvests, and non salty taste to leaves when so watered. The leaves having less than 4.25, 4, 3.75, 3.5, 3.25, 3, 2.75, 2.5, 2.4%, Na content.

Secondary physiological and morphological characteristics are moderate to high resistance to intense continuous grazing, with high resistance or tolerance to leaf and stem diseases, high resistance or tolerance to pathogenic nematodes, and high resistance or tolerance to crown and root diseases, and high drought tolerance. Also a leaf size being intermediate to large, with moderate to very strong stem branching and intermediate to very high stem density. Preferably the secondary physiological characteristics also include a propensity to develop a broad crown ranging from moderate to very strong and forage quality being high to very high.

Example 4

Salt Tolerance in the Glasshouse

Glasshouse Experiment 2010/11

This experiment was devised to explore the limits of tolerance of the varieties developed in Example 2.

SN 2011/1 was the salt tolerant variety tested, and the controls were "Jindera" and "Silverado".

200 of respective seeds were sown into trays of 40 cm by 30 cm to a depth of 1 cm, in garden loam. They were allowed to germinate in glasshouse conditions and grown for 25 days, with tap water. From day 26 plants were watered with either tap water or tap water with NaCl added to 200 mM, 250 mM or 300 mM. Foliage was harvested to a level of 1 cm above the soil four times, H1 at 126 days, H2 at 165 days, H3 at 195 days, and H4 at 225 days. The quantity of foliage harvested was measured as FW (fresh weight), and then dried in a microwave for 2 mins and remeasured as DW (dry weight). A comparison of the weight of the sample of the salt tolerant (ST) plant, Jindera (J) and Silverado (S) were also calculated as a percentage and have been tabulated below.

| | SN 2011/1 | SN 2011/2 | SN 2011/3 |
|---|---|---|---|
| Salinity tolerance | Tolerant to salinity (150 mM Sodium chloride) from the seedling stage up to the mature plant stage | | |
| Salt content of leaves | When grown in soil with at least 150 mM Sodium Chloride, the sodium content of leaves is less than 3% | | |
| Salinity tolerance | All plants have no leaf distortions, paleness, yellowing or necrosing from the commencement of saline treatments until the first harvest (defoliation or on shoots initiated from the crowns of the plants defoliated at 2 cm above the crown while growing in saline soil. | | |
| Autumn (Fall) Dormancy | class 4-5 | Class 6-7 | Classes 8-10 |
| Propensity to develop a broad crown | Very strong | Strong | moderate |
| Resistant to intense continuous grazing | very high | high | moderate |
| Resistance or tolerance to leaf and stem disease | | high | |
| Resistance or tolerance to pathogenic nematodes | | high | |
| Resistance or tolerance to crown and root disease | | high | |
| Drought tolerance | | high | |
| Forage quality | very high | high | high |
| Leaf size | Intermediate | Intermediate | Large |
| Stem Branching | Very strong | strong | moderate |
| Stem Density | very high | high | Intermediate |

Salinity Tolerant Example was SN 2011/1

| | Irrigation Water NaCl concentration | | | | | | | | | | | |
|---|---|---|---|---|---|---|---|---|---|---|---|---|
| | 0 mM | | | 200 mM | | | 250 mM | | | 300 mM | | |
| | C | ST | J | C | ST | J | C | ST | J | C | ST | J |
| FW | | | | | | | | | | | | |
| H1 | 29.85 | 34.25 | 11.70 | 26.15 | 32.05 | 9.70 | 16.80 | 26.35 | 4.10 | 5.95 | 14.45 | 2.35 |
| H2 | 16.60 | 15.35 | 4.30 | 1.10 | 5.45 | 1.00 | 0.90 | 2.85 | 0 | 0 | 0.05 | 0 |
| H3 | 16.40 | 14.35 | 4.00 | 0.50 | 2.55 | 0.15 | 0.15 | 0.30 | 0 | 0 | 0.05 | 0 |
| H4 | 9.45 | 5.40 | 1.05 | 0.15* | 1.15** | 0 | 0.05* | 0.25*** | 0 | 0 | 0 | 0 |
| DW | | | | | | | | | | | | |
| H1 | 4.35 | 5.30 | 1.95 | 5.55 | 5.30 | 1.75 | 2.95 | 4.60 | 0.70 | 1.95 | 4.05 | 0.40 |
| H2 | 3.05 | 2.85 | 0.85 | 0.30 | 1.20 | 0.25 | 0.10 | 0.50 | 0 | 0 | TR | 0 |
| H3 | 3.00 | 2.40 | 0.70 | 0.20 | 0.60 | 0.05 | 0.10 | 0.10 | 0 | 0 | TR | 0 |
| H4 | 1.60 | 0.90 | 0.15 | TR* | 0.20** | 0 | TR* | 0.05*** | 0 | 0 | 0 | 0 |
| % FW | | | | | | | | | | | | |
| H1 | 100 | 123 | 42.0 | 100 | 122.6 | 37.1 | 100 | 156.8 | 24.4 | 100 | 242.9 | 39.5 |
| H2 | 100 | 92.5 | 25.9 | 100 | 495.5 | 90.9 | 100 | 316.7 | 0 | — | n.c. | — |
| H3 | 100 | 87.5 | 24.4 | 100 | 510.0 | 30.0 | 100 | 200 | 0 | — | n.c. | — |
| H4 | 100 | 57.1 | 11.1 | 100 | 766.7 | 0 | 100 | 500 | 0 | — | — | — |
| % DW | | | | | | | | | | | | |
| H1 | 100 | 121.8 | 44.8 | 100 | 95.5 | 31.5 | 100 | 155.9 | 23.7 | 100 | 207.1 | 21.1 |
| H2 | 100 | 93.4 | 27.9 | 100 | 400.0 | 83.3 | 100 | 500 | 0 | — | n.c. | — |
| H3 | 100 | 80.0 | 23.3 | 100 | 300.0 | 25.0 | 100 | 100+ | 0 | — | n.c. | — |
| H4 | 100 | 56.2 | 9.4 | — | n.c. | — | — | n.c. | — | — | — | — |

*residue from necrotic control plants, No control plants survive to harvest 4.
**Yield from 4 plants surviving at harvest 4.
***Yield from 2 plants surviving at harvest 4
n.c. No surviving or insufficient control sample
+An anomalous result
TR denotes - trace Standardised Tolerance to Salt of SN2011/1

| | 0 mM | | | 200 mM | | | 250 mM | | |
|---|---|---|---|---|---|---|---|---|---|
| FW | C | ST | J | C | ST | J | C | ST | J |
| H1 | 100 | 100 | 100 | 100 | 100 | 100 | 100 | 100 | 100 |
| H2 | 55.6 | 44.8 | 36.8 | 7.2 | 37.9 | 11.3 | 9.7 | 24.1 | 0 |
| H3 | 55.6 | 41.9 | 24.2 | 1.9 | 19.1 | 1.5 | 1.6 | 2.6 | 0 |
| H4 | 31.7 | 15.8 | 9.0 | 0.5 | 22.8 | 0 | 0.6 | 6.3 | 0 |

Reduction in yield expressed as a % of yield at H1 for C, ST and J at 200 and 250 mM, adjusted for relative yield at 0 mM. It can be seen that the yield of the salt tolerant example SB 2011/1 at 200 mM is consistent at about 20% of H1 yield extending out from H3, whereas the corresponding yield of the controls reduces to a level approaching zero.

Discussion

As can be seen from Table 1, at 200 mM NaCl, beyond harvest 1 there are significant differences between the salt tolerant test population (ST), the diploid parent (J) and tetraploid parent (C). In harvest 4 there are 57 surviving plants. From visual inspection of experimental trays it is seen that the trends seen for the 200 mM NaCl treated trays are also seen in 150 mM NaCl treated trays. These were not measured in the present experiment.

The yield achieved under various salt treatments are adjusted for the general survival of plants without salt treatment, thus adjusting for the capacity of plants to live in the test conditions of these glass-house conditions. It is anticipated that the proportion of plants surviving the treatment of salt would increase should SN2011/1 be subjected to further selection over several generations, to increase the proportion of plants carrying the salt resistant gene or genes. It is not expected, however, that individual plants in the resulting population would become markedly more resistant to higher levels of salt resistance.

One of the significant differences between surviving plants of the ST population and control populations is that the leaves of surviving controls are salty to taste, whereas the surviving ST plants are vigorous and the leaves do not taste salty. Preliminary mineral content tests show that the Na content of leaves with the non-salty taste is less than about 2.5%, although it is to be understood that this is an approximate value due to the limited number of samples measured.

Samples of leaves from surviving individual plants from various treatments were combined, dried and sent to CSBP Soil and Plant Analysis Laboratory Perth, Western Australia for treatment to provide the following preliminary results. Insufficient material was available from all trays for chemical analysis.

| C 0 | ST 0 | C 100 | ST 100 | C 150 | ST 150 | ST 200 |
|---|---|---|---|---|---|---|
| 1.74% | 0.92% | 4.34% | 2.05% | 4.37% | 1.85% | 2.28% |

C—Control
ST—Salt Tolerant, being SN2011/1

These are preliminary results that applicant intends to confirm using larger samples, and confirm taste testing of the leaves of plants taken from trays treated with 1, 100, 150, 200, 250 and 300 mM NaCl. It was found that by tasting an individual leaf of a surviving plant that leaves of the salt tolerant plant survivors were not salty to taste, whereas leaves of plants of controls that were tasted had a salty taste, once they had been watered with saline water. It is anticipated that where larger leaf samples are taken and tested that the general trend of these results will be confirmed for the remainder of the treatments.

Example 5

Salt Tolerance in the Field

Salt tolerance was tested in Queensland, Australia, in the field, in particular a field having an area of very high salinity bordered by more normal soil. Salinity in affected fields varies considerably, thus in any particular field the salt concentration will usually vary irregularly in a general direction.

Test populations were sown in 5 m row plots at a seeding rate of 1 gram (approximately 400 seeds) per row. The test population was taken from about 72 survivors of selection cycle 6F. It might be noted that these were the parent population of SB 2011/1 (see intercrossing cycle 6F). Test rows were inter-seeded with rows of the variety "Silverado" as a control. The Silverado rows were taken to have the same soil sodium content as the immediately adjacent salt tolerant rows.

Selected soil samples were sent to CSBP testing laboratories to measure inter alia soil conductivity. The results are as follows:

| | Soil Salinity | | Plant Density* | | Regrowth** | |
|---|---|---|---|---|---|---|
| Site | dS/m | NaCl mM/L*** | Silverado | Silverosa† | Silverado | Silverosa† |
| 1 | 4.54 | 49.71 | 17 (10-30) | 43 (20-60)ƒ | 40 | 37 (20-50) |
| 2 | 9.04 | 98.99 | 7 (0-20) | 43 (26-70) | 0 | 15 (10-30) |
| 3 | 11.82 | 129.43 | 0 | 38 (10-70) | 0 | 12 (10-20) |
| 4 | 12.48 | 136.66 | 0 | 10 (0-20) | 0 | 6 (0-10) |
| 5 | 39.70 | 434.72 | 0 | 0 | 0 | 0 |

*% of initial number of viable seeds per row 14 months after sowing
**relative regrowth compared with plants growing in very low salinity
***(dS/m x 10.95)
†Population tested in Selection Cycle 6F (see example 2)
ƒRange of scores of progeny rows within 1.2 m of a Silverado (Control) row selected as a soil sampling site.

Discussion

Site 1 is slightly affected by salinity but the Silverado control plants survived.

Site 2 represents the boundary of survival by the Silverado control.

Site 3 is too salty for the control but test plants survived. Individual plants were severely to only moderately affected by salinity (density range 10 to 70).

Site 4 is yet more severe. Survival of test plants ranged from no tolerant (survival 0%) to moderately tolerant (survival 20%)

Site 5 was an extremely saline site, where no plants survived.

Example 6

Salt Tolerance in the Glass House

Glasshouse Experiment 2010/11

This experiment was devised to repeat Example 4 except to extend the range of salt treatments and plants tested including putative salt tolerant lucerne Salado.

All three lines of Silverosa were used namely SN 2011/1, SN 2011/2 and SN 2011/3. Controls used were Jindera, Salado and Silverado.

All except Salado were grown in 3 rows per plot at 0.2 g/row. With Salado because there were limited seeds available only 1 row was grown at the same rate. Two set of plots were made for each sample Respective seeds were sown into trays of 40 cm by 30 cm to a depth of 1 cm, in garden loam. They were allowed to germinate in glasshouse conditions and grown for 40 days, with tap water. From day 40 plants were watered with either tap water or tap water with NaCl added to 100 mM, 150 mM, 200 mM, 250 mM or 300 mM. Foliage was harvested to a level of 1 cm above the soil four times, H1 at 78 days, H2 at 118 days, H3 at 158 days, and H4 at 204 days. The quantity of foliage harvested was measured as FW (fresh weight, in grams), and then dried in a microwave for 2 mins and remeasured as DW (dry weight, in grams) the number of plant were counted for each plot and divided by 2 (No.). A comparison of the weight of the harvested sample for both plots for each type of plant were also calculated as a percentage and have been tabulated below.

|  |  | Population | | | | | | | | |
|---|---|---|---|---|---|---|---|---|---|---|
|  |  | SN2011/1 | | | SN2011/2 | | | SN2011/3 | | |
|  |  | | | | Character | | | | | |
| NaCl (mM) | Harvest | FW | DW | No. | FW | DW | No. | FW | DW | No. |
| 0 | H1 | 29.30 | 5.10 | 126.5 | 25.75 | 4.75 | 97.5 | 24.60 | 4.45 | 118.0 |
|  | H2 | 11.55 | 2.35 | 120.5 | 9.2 | 1.95 | 94.0 | 10.95 | 2.35 | 116.0 |
|  | H3 | 4.85 | 1.05 | 96.0 | 5.35 | 1.25 | 68.0 | 5.95 | 1.40 | 73.0 |
|  | H4 | 2.25 | 1.00 | 67.5 | 2.90 | 0.55 | 38.0 | 3.95 | 0.65 | 48.0 |
| 100 | H1 | 18.70 | 3.75 | 114.5 | 21.00 | 3.95 | 125.0 | 20.30 | 3.75 | 100.5 |
|  | H2 | 5.60 | 1.20 | 48.0 | 10.25 | 2.10 | 101.5 | 8.45 | 1.60 | 51.0 |
|  | H3 | 0.95 | 0.25 | 16.0 | 2.85 | 0.75 | 35.0 | 0.80 | 0.20 | 16.5 |
|  | H4 | 0.3 | 0.05 | 5.5 | 1.05 | 0.15 | 12.5 | 0.25 | 0.05 | 12.0 |
| 150 | H1 | 14.00 | 2.90 | 132.5 | 19.80 | 4.15 | 160.0 | 16.10 | 3.15 | 129.5 |
|  | H2 | 5.55 | 1.10 | 97.0 | 2.55 | 0.50 | 101.0 | 4.65 | 1.00 | 94.0 |
|  | H3 | 0.75 | 0.20 | 24.5 | 0.90 | 0.25 | 33.0 | 1.45 | 0.45 | 33.0 |
|  | H4 | 0.30 | 0.10 | 8.0 | 0.30 | 0.05 | 5.0 | 0.55 | 0.05 | 13.0 |
| 200 | H1 | 17.95 | 3.90 | 131.0 | 10.60 | 2.40 | 151.5 | 14.25 | 2.80 | 141.0 |
|  | H2 | 1.95 | 0.45 | 51.5 | 4.05 | 0.95 | 116.5 | 4.60 | 1.00 | 94.0 |
|  | H3 | 0.70 | 0.20 | 20.5 | 1.70 | 0.50 | 32.0 | 1.60 | 0.40 | 36.0 |
|  | H4 | 0.20 | 0.05 | 8.5 | 0.10 | <0.05 | 10.0 | 0.25 | 0.05 | 11.0 |
| 250 | H1 | 14.55 | 3.45 | 145.5 | 10.25 | 2.35 | 104.5 | 11.15 | 2.40 | 123.5 |
|  | H2 | 1.25 | 0.25 | 54.5 | 1.45 | 0.35 | 30.0 | 0.85 | 0.25 | 36.5 |
|  | H3 | 0.20 | 0.05 | 8.5 | 0.15 | 0.05 | 7.5 | 0.10 | <0.05 | 6.5 |
|  | H4 | 0 | 0 | 3.0 | 0 | 0 | 0 | 0 | 0 | 2.0 |
| 300 | H1 | 11.85 | 3.15 | 158.5 | 16.25 | 3.70 | 152.5 | 12.00 | 3.15 | 136.5 |
|  | H2 | 0.30 | 0.10 | 76.0 | 1.45 | 0.4 | 81.0 | 0.65 | 0.15 | 44.5 |
|  | H3 | 0 | 0 | 1.0 | 0.25 | 0.10 | 11.5 | 0.1 | <0.05 | 5.0 |
|  | H4 | 0 | 0 | 0 | 0.1 | 0.05 | 2.0 | 0.2 | 0.05 | 2.0 |

|  |  | Population | | | | | | | | |
|---|---|---|---|---|---|---|---|---|---|---|
|  |  | Jindera | | | Salado | | | Silverado | | |
|  |  | | | | Character | | | | | |
| NaCl (mM) | Harvest | FW | DW | No. | FW | DW | No. | FW | DW | No. |
| 0 | H1 | 9.35 | 1.90 | 72.5 | 4.70 | 0.80 | 14.5 | 30.80 | 5.20 | 131.5 |
|  | H2 | 1.95 | 0.40 | 60.5 | 2.05 | 0.40 | 13.5 | 10.00 | 2.00 | 127.5 |
|  | H3 | 1.20 | 0.30 | 26.0 | 1.20 | 0.20 | 11.0 | 6.55 | 1.45 | 83.5 |
|  | H4 | 0.30 | 0.05 | 7.0 | 0.80 | 0.15 | 9.0 | 2.50 | 0.50 | 54.5 |
| 100 | H1 | 3.55 | 0.80 | 83.0 | 2.65 | 1.20 | 9.5 | 23.05 | 4.25 | 135.0 |
|  | H2 | 0.35 | 0.10 | 5.0 | 1.25 | 0.25 | 4.0 | 8.20 | 1.85 | 93.5 |
|  | H3 | 0 | 0 | 0 | 0.1 | <0.1 | 0.5 | 2.25 | 0.55 | 29.5 |
|  | H4 | 0 | 0 | 0 | 0 | 0 | 0 | 0.75 | 0.15 | 8.5 |
| 150 | H1 | 5.00 | 1.10 | 85.0 | 1.70 | 0.35 | 11.5 | 18.10 | 3.85 | 164.5 |
|  | H2 | 0.45 | 0.10 | 31.5 | 0.20 | <0.10 | 1.0 | 3.65 | 0.75 | 73.0 |
|  | H3 | 0 | 0 | 0 | 0 | 0 | 0 | 0 | 0 | 0 |
|  | H4 | 0 | 0 | 0 | 0 | 0 | 0 | 0 | 0 | 0 |
| 200 | H1 | 4.20 | 1.00 | 69.5 | 1.30 | 0.25 | 13.5 | 19.50 | 4.15 | 157.0 |
|  | H2 | 0.35 | <0.1 | 3.5 | 0.3 | <0.1 | 3.5 | 2.65 | 0.55 | 55.5 |
|  | H3 | 0 | 0 | 0 | 0 | 0 | 0 | 0 | 0 | 0 |
|  | H4 | 0 | 0 | 0 | 0 | 0 | 0 | 0 | 0 | 0 |
| 250 | H1 | 4.24 | 0.95 | 83.0 | 2.30 | 0.45 | 13.5 | 16.85 | 3.85 | 169.5 |
|  | H2 | <0.05 | <0.05 | 5.0 | 0.25 | 0.10 | 3.0 | 1.40 | 0.35 | 42.0 |
|  | H3 | 0 | 0 | 0 | 0 | 0 | 0 | 0 | 0 | 0 |
|  | H4 | 0 | 0 | 0 | 0 | 0 | 0 | 0 | 0 | 0 |
| 300 | H1 | 2.55 | 0.60 | 79.0 | 2.35 | 0.55 | 10.0 | 14.05 | 3.40 | 168.0 |
|  | H2 | 0 | 0 | 0 | 0.55 | 0.10 | 2.0 | 0.45 | 0.10 | 67.0 |
|  | H3 | 0 | 0 | 0 | 0 | 0 | 0 | 0 | 0 | 0 |
|  | H4 | 0 | 0 | 0 | 0 | 0 | 0 | 0 | 0 | 0 |

|  |  | Population | | | | | | | | |
|---|---|---|---|---|---|---|---|---|---|---|
|  |  | SN1 | | | SN2 | | | SN3 | | |
| NaCl |  | | | | Character | | | | | |
| (mM) | Harvest | FW | DW | No. | FW | DW | No. | FW | DW | No. |
| 0 | H1 | 100 | 100 | 100 | 100 | 100 | 100 | 100 | 100 | 100 |
|  | H2 | 39.42 | 46.08 | 95.26 | 35.73 | 41.05 | 96.41 | 44.51 | 52.81 | 98.31 |

-continued

| | | Population | | | | | | | | |
|---|---|---|---|---|---|---|---|---|---|---|
| | | SN1 | | | SN2 | | | SN3 | | |
| NaCl | | | | | Character | | | | | |
| (mM) | Harvest | FW | DW | No. | FW | DW | No. | FW | DW | No. |
| | H3 | 16.55 | 20.59 | 75.89 | 20.78 | 26.32 | 69.74 | 24.19 | 31.46 | 61.86 |
| | H4 | 7.69 | 19.61 | 53.36 | 11.26 | 11.58 | 38.97 | 16.06 | 14.61 | 40.68 |
| 100 | H1 | 100 | 100 | 100 | 100 | 100 | 100 | 100 | 100 | 100 |
| | H2 | 29.94 | 32.0 | 41.92 | 48.81 | 53.16 | 81.20 | 41.63 | 42.67 | 50.75 |
| | H3 | 5.08 | 6.67 | 13.97 | 13.57 | 18.99 | 28.00 | 3.94 | 5.33 | 16.42 |
| | H4 | 1.60 | 1.33 | 4.80 | 0.05 | 3.80 | 10.00 | 1.23 | 1.33 | 11.94 |
| 150 | H1 | 100 | 100 | 100 | 100 | 100 | 100 | 100 | 100 | 100 |
| | H2 | 39.64 | 37.93 | 73.21 | 12.88 | 12.05 | 63.13 | 28.89 | 31.75 | 72.59 |
| | H3 | 5.35 | 6.90 | 18.49 | 4.55 | 6.02 | 20.62 | 9.01 | 14.29 | 25.48 |
| | H4 | 2.14 | 3.45 | 6.04 | 1.52 | 1.20 | 3.13 | 3.42 | 1.59 | 10.04 |
| 200 | H1 | 100 | 100 | 100 | 100 | 100 | 100 | 100 | 100 | 100 |
| | H2 | 10.86 | 11.53 | 39.31 | 38.21 | 39.58 | 76.90 | 32.28 | 35.71 | 66.67 |
| | H3 | 3.90 | 5.13 | 15.65 | 16.04 | 20.83 | 21.12 | 11.23 | 14.29 | 25.53 |
| | H4 | 1.11 | 1.28 | 6.49 | 0.94 | <2.08 | 6.60 | 1.75 | 1.79 | 7.80 |
| 250 | H1 | 100 | 100 | 100 | 100 | 100 | 100 | 100 | 100 | 100 |
| | H2 | 8.59 | 7.24 | 37.46 | 14.15 | 14.89 | 28.71 | 7.62 | 10.42 | 29.55 |
| | H3 | 1.37 | 1.45 | 5.84 | 1.46 | 2.13 | 7.18 | 0.90 | <2.08 | 5.26 |
| | H4 | 0 | 0 | 2.06 | 0 | 0 | 0 | 0 | 0 | 1.62 |
| 300 | H1 | 100 | 100 | 100 | 100 | 100 | 100 | 100 | 100 | 100 |
| | H2 | 2.53 | 3.17 | 47.95 | 8.92 | 10.81 | 53.11 | 5.42 | 4.76 | 32.60 |
| | H3 | 0 | 0 | 0.63 | 1.54 | 2.70 | 7.54 | 0.83 | <1.58 | 3.67 |
| | H4 | 0 | 0 | 0 | 0.62 | 1.35 | 1.31 | 1.67 | 1.58 | 1.47 |

| | | Population | | | | | | | | |
|---|---|---|---|---|---|---|---|---|---|---|
| | | Jindera | | | Salado | | | Silverado | | |
| NaCl | | | | | Character | | | | | |
| (mM) | Harvest | FW | DW | No. | FW | DW | No. | FW | DW | No. |
| 0 | H1 | 100 | 100 | 100 | 100 | 100 | 100 | 100 | 100 | 100 |
| | H2 | 20.86 | 21.05 | 83.45 | 43.62 | 50.00 | 93.10 | 32.46 | 38.46 | 96.96 |
| | H3 | 12.83 | 15.79 | 35.86 | 25.53 | 25.00 | 75.86 | 21.27 | 27.88 | 63.50 |
| | H4 | 3.21 | 2.63 | 9.66 | 17.02 | 18.75 | 62.07 | 8.12 | 9.62 | 41.44 |
| 100 | H1 | 100 | 100 | 100 | 100 | 100 | 100 | 100 | 100 | 100 |
| | H2 | 9.86 | 12.5 | 6.02 | 47.17 | 20.83 | 42.1 | 35.57 | 43.53 | 69.26 |
| | H3 | 0 | 0 | 0 | 3.77 | 8.33 | 5.26 | 9.64 | 12.94 | 21.85 |
| | H4 | 0 | 0 | 0 | 0 | 0 | 0 | 3.25 | 3.53 | 6.30 |
| 150 | H1 | 100 | 100 | 100 | 100 | 100 | 100 | 100 | 100 | 100 |
| | H2 | 9.00 | 10.00 | 37.06 | 11.76 | <20.0 | 8.70 | 20.17 | 19.48 | 44.38 |
| | H3 | 0 | 0 | 0 | 0 | 0 | 0 | 0 | 0 | 0 |
| | H4 | 0 | 0 | 0 | 0 | 0 | 0 | 0 | 0 | 0 |
| 200 | H1 | 100 | 100 | 100 | 100 | 100 | 100 | 100 | 100 | 100 |
| | H2 | 8.33 | <10.0 | 5.03 | 23.08 | <20.00 | 25.92 | 13.59 | 13.25 | 35.35 |
| | H3 | 0 | 0 | 0 | 0 | 0 | 0 | 0 | 0 | 0 |
| | H4 | 0 | 0 | 0 | 0 | 0 | 0 | 0 | 0 | 0 |
| 250 | H1 | 100 | 100 | 100 | 100 | 100 | 100 | 100 | 100 | 100 |
| | H2 | <1.18 | <5.26 | 6.02 | 10.87 | 22.22 | 22.22 | 8.31 | 9.09 | 24.78 |
| | H3 | 0 | 0 | 0 | 0 | 0 | 0 | 0 | 0 | 0 |
| | H4 | 0 | 0 | 0 | 0 | 0 | 0 | 0 | 0 | 0 |
| 300 | H1 | 100 | 100 | 100 | 100 | 100 | 100 | 100 | 100 | 100 |
| | H2 | 0 | 0 | 0 | 23.40 | 18.18 | 20.0 | 3.20 | 2.94 | 39.88 |
| | H3 | 0 | 0 | 0 | 0 | 0 | 0 | 0 | 0 | 0 |
| | H4 | 0 | 0 | 0 | 0 | 0 | 0 | 0 | 0 | 0 |

In summary it can be seen that the parent Jindera is very sensitive to salt, with no survivors past the second harvest at 100 mM NaCl. For Salado the survivors carried through to the third harvest at 100 mM, however at 150 mM there were no survivors past the second harvest. Silverado was slightly more robust than Salado in that survivors carried through to the fourth harvest at 100 mM whereas there were no survivors past the second harvest at 150 mM.

All three lines of the Silverosa had survivors through to the 4th harvest at 200 mM and 3rd harvest at 250 mM NaCl. At 300 mM NaCl SN2 and SN3 had survivors through to the 4th harvest, at 350 mM NaCl there were no survivors past the second harvest (results not shown).

There is therefore a significantly greater tolerance to salt with all three lines of Silverosa compared to parent plants Jindera and Silverado, and also significantly more resistance to Salado, the putative salt tolerant variety. Significant differences can be seen in the tests conducted at 150 mM, 200 mM, 250 mM and 300 mM NaCl.

With regards to the Salado the data presented above support the data of Peel et al., (2004) that Salado does not appear to exhibit any significant degree of salt tolerance, at least relative to Jindera and Silverado.

Cell and Tissue Culture of Lucerne

Further reproduction of the lucerne varieties of the present invention can occur by cell and tissue culture and regeneration. Thus, another aspect of this invention is to provide cells which upon growth and differentiation produce lucerne plants which are salt tolerant. Yet another embodiment is a tissue culture of regenerable cells, where the cells include genetic material that convey salt tolerance to lucerne plants. Some embodiments include such a tissue culture that includes cultured cells derived, in whole or in part, from a plant part selected from the group consisting of leaves, roots, root tips, root hairs, anthers, pistils, stamens, pollen, ovules, flowers, pods, seeds, embryos, leaves, stems, buds, cotyledons, hypocotyls, cells and protoplasts.

In one embodiment, this invention provides cells which upon growth and differentiation produce lucerne plants having all or substantially all of the physiological and morphological characteristics of alfalfa varieties SN 2011/1, SN 2011/2 and SN 2011/3.

Methods of producing lucerne plants from tissue culture are well known by the ordinary artisan.

Initiation of callus from immature anthers, immature ovaries, cotyledons, internode sections, and seedling hypocotyls of SN 2011/1, SN 2011/2 and SN 2011/3 can be achieved on Blaydes medium supplemented with various combinations and concentrations of kinetin (K), □□-naphthalene acetic acid (NAA), and 2,4-dichlorophenoxyacetic acid (2,4-D). See, for example, Saunders, J. and E. T. Bingham, Crop Science 12(6):804-808 (1972). Whole lucerne plants can be produced from the callus tissue, wherein the lucerne plants have the same or substantially the same morphological and physiological characteristics as the plant from which the calli were derived.

Various features of the invention have been particularly shown and described in connection with the exemplified embodiments of the invention, however, it must be understood that these particular arrangements merely illustrate and that the invention is not limited thereto. Accordingly the invention can include various modifications, which fall within the spirit and scope of the invention. It should be further understood that for the purpose of the specification the word "comprise" or "comprising" means "including but not limited to".

The invention claimed is:

1. A *Medicago sativa* seed designated as a "Silverosa" representative seed of which having been deposited under NCIMB Accession No. 41909, NCIMB Accession No. 41910 and NCIMB Accession No. 41911.

2. The *Medicago sativa* seed designated as Silverosa, wherein a sample of said seed has been deposited as NCIMB 41910.

3. The *Medicago sativa* seed designated as Silverosa, wherein a sample of said seed has been deposited as NCIMB 41911.

4. A plant or plant parts thereof produced by growing the seed of claim 1.

5. A *Medicago sativa* plant having all the physiological and morphological characteristics of the plant of claim 4.

6. A method of producing a salt tolerant lucerne plant derived from the cultivar "Silverosa" comprising:
    (a) crossing a "Silverosa" plant grown from seed deposited under NCIMB Accession No. 41909, NCIMB Accession No. 41910 or NCIMB Accession No. 41911 with a second lucerne plant to yield progeny lucerne seed; and
    (b) growing said progeny seed to yield a lucerne cultivar Silverosa-derivative plant.

7. The method of claim 6, further comprising:
    (c) crossing the lucerne cultivar Silverosa-derivative plant of (b) with itself or a third lucerne plant to yield seed of a second lucerne Silerosa-derivative; and
    (d) growing the second lucerne Silverosa-derivative seed of (c) to yield a second lucerne cultivar Silverosa-derivative plant.

8. The method of claim 7, wherein steps (c) and (d) are repeated at least once to generate additional Silverosa-derived lucerne plants.

* * * * *